US011657733B2

(12) United States Patent
Xue et al.

(10) Patent No.: US 11,657,733 B2
(45) Date of Patent: May 23, 2023

(54) TRAINING METHOD FOR EVALUATING BONDING ACCURACY OF ORTHODONTIC BRACKETS (71) Applicant: Sichuan University, Chengdu (CN)

(72) Inventors: Chaoran Xue, Chengdu (CN); Peiqi Wang, Chengdu (CN); Bin Li, Chengdu (CN); Ding Bai, Chengdu (CN); Xianglong Han, Chengdu (CN); Hui Xu, Chengdu (CN); Rui Shu, Chengdu (CN); Yongwen Guo, Chengdu (CN); Ye Tian, Chengdu (CN); Jie Feng, Chengdu (CN); Yating Wang, Chengdu (CN)

(73) Assignee: Sichuan University, Chengdu (CN)

( * ) Notice: Subject to any disclaimer, the term of this patent is extended or adjusted under 35 U.S.C. 154(b) by 0 days.

(21) Appl. No.: 17/566,793

(22) Filed: Dec. 31, 2021

(65) Prior Publication Data
US 2022/0215778 A1 Jul. 7, 2022

(30) Foreign Application Priority Data

Jan. 6, 2021 (CN) .......................... 202110010740.3

(51) Int. Cl.
*G09B 23/28* (2006.01)
*A61B 6/03* (2006.01)
*A61C 7/16* (2006.01)
*A61C 9/00* (2006.01)
*A61C 13/34* (2006.01)

(52) U.S. Cl.
CPC ............ *G09B 23/283* (2013.01); *A61B 6/032* (2013.01); *A61C 7/16* (2013.01); *A61C 9/0046* (2013.01); *A61C 13/34* (2013.01)

(58) Field of Classification Search
CPC ......... G09B 23/283; A61B 6/032; A61C 7/16; A61C 7/002; A61C 9/0046; A61C 13/34
See application file for complete search history.

(56) References Cited

U.S. PATENT DOCUMENTS

| 2011/0207072 A1* | 8/2011 | Schiemann | ............ | A61C 7/146 700/98 |
| 2019/0015177 A1* | 1/2019 | Elazar | .................... | G16H 30/40 |

FOREIGN PATENT DOCUMENTS

CN 200951125 Y 9/2007

* cited by examiner

*Primary Examiner* — Cris L. Rodriguez
*Assistant Examiner* — Drew S Folgmann
(74) *Attorney, Agent, or Firm* — Bayramoglu Law Offices LLC (57) ABSTRACT A training method for evaluating the bonding accuracy of orthodontic brackets is provided. The evaluation method includes a training device for racket bonding accuracy evaluation which includes virtual teeth with root-shaped connectors and an evaluation base to fix the virtual teeth. Multiple reference lines are marked on the evaluation base, and their intersection is set as the evaluation point. When the virtual tooth is fixed to the evaluation base, the reference lines and the evaluation points are utilized for rapid evaluation of the bonding accuracy of the bracket. Moreover, thanks to their horizontal arrangement, when there are multiple virtual teeth, the evaluation of bracket bonding would be more intuitive and efficient than using the traditional articulator.

7 Claims, 8 Drawing Sheets

TRAINING METHOD FOR EVALUATING BONDING ACCURACY OF ORTHODONTIC BRACKETS

CROSS REFERENCE TO THE RELATED APPLICATIONS

This application is based upon and claims priority to Chinese Patent Application No. 202110010740.3, filed on Jan. 6, 2021, the entire contents of which are incorporated herein by reference.

TECHNICAL FIELD

Embodiments of the present invention belong to the technical field of orthodontics, and in particular, relate to a training method for evaluating the bonding accuracy of orthodontic brackets. It is specially targeted to the convenient and rapid evaluation of the bonding accuracy of orthodontic brackets in orthodontic training.

BACKGROUND

Currently, the fixed appliance is the most widely used and reliable clinical orthodontic technique. Brackets constitute an indispensable component of fixed appliance treatment, transmitting the force generated by the archwire to the teeth and thus controlling the three-dimensional (3D) tooth movement in the implementation of different techniques such as edge-wise technique, straight-wire technique, or individualized orthodontics. It is vital to accurately bond the brackets since accurate bonded brackets can significantly simplify the treatment process and improve the treatment efficiency, whereas the deviated brackets may prolong the treatment and increase the treating difficulty. Therefore, it is necessary to evaluate the accuracy of bracket bonding in the process of orthodontic training. In the current system of orthodontic training, in vitro simulated brackets are usually used for training and evaluation, e.g., the Chinese utility model patent "Magnetic Orthodontic Bracket Positioning Trainer" (application number: 200620021144.6) in which the simulated teeth are fixed on the articulator for bracket bonding training. However, training systems with standard dentition cannot prepare the trainees for complex situations or individualized malocclusion in clinical practice.

In recent years, 3D technologies such as 3D scanning and 3D printing have facilitated the high-precision acquisition of individualized dental data and simulation of the dental status, providing accuracy, efficiency, and safety during treatment. The techniques can also be applied to orthodontic training to make up for the shortcomings of the current standardized teaching.

However, it remains challenging to evaluate the accuracy of trainees' bracket bonding with efficiency, effectiveness, and stability. On the one hand, the evaluation involves a thorough estimate of the distinctly shaped teeth from multiple directions, and is, therefore, time-consuming and hard to accomplish due to the limited trainers. On the other hand, the reproducibility of the evaluation is doubtful since the procedure mainly relies on the trainer's experience with their naked eyes or the scales.

Therefore, a training method for accuracy evaluation of bracket bonding with high efficiency and effectiveness would greatly facilitate the training of bracket bonding and help cultivate better next-generation orthodontics.

SUMMARY

The present invention provides a training-aiding method for the accuracy evaluation of bracket bonding in vitro. As the method provides rapid evaluation of bracket bonding, it can be widely applied during orthodontic training.

The invention is realized by a technical protocol including the following technical methods:

a bracket bonding accuracy evaluation method including:

a training device for evaluating the bonding accuracy of orthodontic brackets, which includes virtual teeth with root-shaped connectors and an evaluation base to fix the virtual teeth;

the virtual tooth with root-shaped connector includes a virtual crown and a root-shaped connector fixed to the crown, wherein the virtual crown has the same shape as human tooth crown and has a standard bonding region (SBR) marked on it; the root-shaped connector is merged to the virtual crown at ±1 mm from the cemento-enamel junction (CEJ), and the long axis of the connector is parallel to the tooth long axis;

the evaluation base includes connecting grooves to fix the virtual teeth, and reference lines for evaluation, wherein the connecting grooves match with the root-shaped connectors;

the virtual tooth is fixed to the evaluation base through the connection between the root-shaped connector and the connecting groove, and when there are multiple virtual teeth, they are horizontally arranged, and the crown surfaces used for bracket bonding face the same direction;

the reference lines include horizontal reference lines, vertical reference lines, and tooth long axis (TA) reference lines, wherein the TA reference lines are parallel to the long axes of the corresponding virtual teeth fixed to the evaluation base; the intersection of the horizontal reference line and the extended line of the TA reference line defines the evaluation point, and the evaluation point overlaps with the SBR center of each virtual tooth;

the evaluation method includes steps to:

(1) fix the virtual tooth to the matching dental base;

(2) bond the bracket on the fixed virtual tooth from step (1);

(3) remove virtual tooth bonded with bracket from the dental base, and fix it to the corresponding connecting groove on the evaluation base;

(4) determine the center point of the bonded bracket on the fixed virtual tooth, wherein the translation is defined by the distance between the center point of the bonded bracket and the evaluation point, and the rotation is defined by the angle between the vertical bracket slot and the TA reference line;

(5) evaluate bracket bonding accuracy based on the values of translation and rotation;

or (1) fix the virtual tooth to the corresponding connecting groove on the evaluation base;

(2) bond the bracket on the fixed virtual tooth from step (1);

(3) determine the center point of the bonded bracket on the fixed virtual tooth, wherein the translation is defined by the distance between the center point of the bonded bracket and the evaluation point, and the rotation is defined by the angle between the vertical bracket groove and the TA reference line;

(4) evaluate bracket bonding accuracy based on the values of translation and rotation.

It should be noted that when the virtual tooth is fixed to the evaluation base, the reference lines and the evaluation point can be used to evaluate the accuracy of the bonded bracket. Moreover, when there are multiple virtual teeth, as the teeth are horizontally arranged in a line, the device provides a more intuitive view of the bonded brackets than traditional training articulators in the shapes of the dental arches.

Generally speaking, the reference lines used for evaluation and the evaluation point defined by the intersection of different reference lines are determined by the existing bracket bonding standards. When the virtual tooth is fixed to the evaluation base, extended lines of the reference lines pass through the SBR, and the evaluation point overlaps with the SBR center.

It should be noted that the bracket bonding standards mentioned before refer to the standards that are implemented in the fixed orthodontic technique. Generally speaking, bracket bonding standards of any orthodontic technique that include a combination of brackets and archwires or standards summarized through experience can be applied to the determination of the reference line in the present invention.

To better explain the present invention and provide a feasible technical protocol, the SBR is defined as a rectangular area designated by 2 mm up, down, left, and right from the center point of the labial or buccal surface of the virtual tooth based on Andrews and MBT bracket bonding standards, two standards that are universally applied nationwide. The extended lines of the reference lines pass through the SBR center, and the evaluation point overlaps with the SBR center. Notably, in the evaluation view, the extended lines of the reference lines also pass through the SBR center, and the evaluation point also overlaps with the SBR center.

Further, the reference lines include horizontal reference lines, vertical reference lines, and tooth long axis (TA) reference lines, wherein the TA reference lines are parallel to the long axes of the corresponding virtual teeth fixed to the evaluation base. The intersection of the horizontal reference line and the extension of the TA reference line defines the evaluation point. The evaluation point overlaps with the SBR center of each virtual tooth, or the two points overlap from the view of evaluation.

The area of SBR exceeds the area of bracket bonding under the guidance of Andrews and MBT bracket bonding standards. The translation of the bracket bonding is considered qualified when the edges of the bracket are within the SBR, i.e., the center of the bracket deviates from the evaluation point by less than 1 mm. Meanwhile, the rotation is considered qualified when the vertical slot of the bracket is parallel to or overlaps with the TA reference line or its extension. If the translation and rotation of the bracket are both considered qualified, then the bracket can be regarded as accurately bonded.

To better perform the evaluation, the trainer utilizes the reference lines in the evaluation view which refers to a horizontal head-up view in most situations. The virtual teeth are fixed to the connecting grooves on the evaluation base. To guarantee the same directions of the crown surfaces for brackets bonding, the angles between the center lines of the connecting grooves and the vertical reference lines can be adjusted according to the type of the virtual teeth. The angles range from 0° to 20° for anterior teeth and 15° to 45° for posterior teeth.

Further, in addition to fixing the virtual tooth and providing evaluation references, the evaluation base can be shaped differently based on actual educational needs and costs. Considering the cost of the model, the aforementioned preferred view of evaluation, and the horizontally arranged virtual teeth, the evaluation base is in the shape of a cuboid with connecting grooves to fix the virtual tooth on the top surface and reference lines for evaluation on the lateral surfaces.

Wherein, to prevent the virtual tooth model from rotating in the connecting groove when fixed on the evaluation base and fix the virtual tooth model in its corresponding connecting groove without confusion, the cross-section of the root-shaped connector is designed to be irregular and distinct from each other.

Further, to fix the virtual tooth more conveniently, the cross-sectional shape of the root-shaped connector is in accordance with that of the virtual tooth at ±1 mm from the CEJ along the tooth long axis, and the length of the root-shaped connector is 10-15 mm along the tooth long axis. Generally speaking, the virtual tooth is cut 0-1 mm apically from the CEJ to keep the integrity of the virtual crown.

Preferably, to facilitate the magnetic retention of the virtual tooth, the tooth root connector has a hollow structure with a 0.5-2 mm-thick wall, and the opening on the apical side of the connector can be used to fill magnetic materials. Correspondingly, the bottom of the connecting groove of the evaluation base is also embedded with magnetic materials.

Generally speaking, when the present device is used to evaluate the bonding accuracy, the virtual tooth is bonded with the brackets and fixed on the evaluation base. The accuracy is evaluated based on the distance between the center point of the brackets and the evaluation point and the angle between the vertical bracket slot and the TA reference line. In this way, the device can be utilized even when only one bracket is evaluated. However, in consideration of efficiency and clinical practice where 14 teeth in each dentition are often bonded at the same time, preferably, the virtual teeth with root-shaped connectors had the shapes of human teeth and are arranged on the evaluation base in the original adjacent relations with an amount of 3-14.

It is worth noting that the inventors of the present invention have noticed that, in the case of a horizontal head-up view of evaluation, especially when using the evaluation methods by horizontal camera shoot, it is most suitable to evaluate the 3 or 6 virtual teeth at the same time. When there are three virtual teeth, the teeth are usually three anterior teeth or three posterior teeth (except the second molars). This is because bracket bonding of the anterior and posterior teeth requires different perspectives when operated in the mouth, and the bonding accuracy is therefore affected to a certain extent. Also, it is conventional to classify the dentition according to the anterior and posterior regions. When there are six virtual teeth, they are adjacent anterior teeth, e.g., 11, 12, 13, 21, 22, and 23 or 31, 32, 33, 41, 42, and 43. The six anterior teeth are aesthetic-related teeth that affect facial attractiveness upon smiling or mouth opening. The accuracy of bracket bonding position affects the final position and inclination angle of the anterior teeth, thereby affecting the patient's appearance.

Preferably, to facilitate the setting of reference lines for evaluation on the evaluation base, side walls are built bilateral to the connecting grooves, marked with reference lines for evaluation. Generally speaking, the reference lines marked on the side walls are reference lines for alignment.

Further, to facilitate evaluation, the reference lines on the side walls include horizontal reference lines marked from the horizontal view and vertical reference lines marked from the vertical view.

Wherein, the TA reference line is set on the evaluation base and located at or below the corresponding position of the connecting groove on the top surface.

Preferably, to facilitate the setting of reference lines on the evaluation base, the evaluation base is also provided with an auxiliary transparent plate marked with evaluation reference lines or reference colored stamps. The colored stamps are used to evaluate the bonding accuracy of the brackets since they overlap with the corresponding SBR.

Generally speaking, the virtual crowns are physical models with the sizes of the real crowns. They are 3D printed from digital models obtained from 3D scanning of the deformed teeth of actual patients. It is worth noting that the virtual crowns in the present invention constitute a digital model of human teeth. Therefore, complex cases that are difficult to treat in clinical treatment, such as crowded dentitions, can also be applied to the present invention for quick evaluation after bracket bonding training.

To better illustrate the present invention and provide a preferable technical protocol, the evaluation base is a cuboid with a length of 5-80 mm, a width of 5-30 mm, and a height of 13-40 mm with connection grooves on the top surface and side walls with a height of 7-15 mm bilateral to the connecting grooves.

With the preferred technical protocol, the accuracy of the bracket bonding can be easily and quickly evaluated through the horizontal reference lines, the vertical reference lines, and the TA reference lines, The method of the present invention is applied to brackets used in the edge-wise technique, straight-wire technique, individualized brackets, any other orthodontic accessories including buccal tubes, as well as bonding training in different types of malocclusion with the aid of the virtual teeth and the evaluation base.

It should be noted that in the practical manufacture of the present embodiments, the first step is to determine the patient to be selected and obtain the digital tooth model by 3D scanning the deformed teeth of the patient. The SBR can be determined in 3D software according to the actual situation or by the following steps: 3D printing of the virtual teeth, standard bonding by orthodontic experts, 3D scanning of the virtual teeth bonded with brackets, and SBR determination according to the scanned teeth with the bonded brackets.

Subsequently, the 3D model of the evaluation base is established in 3D software, the 3D virtual teeth are horizontally arranged with their SBRs on the same horizontal line and the root-shaped connectors fixed to the connecting grooves, and the horizontal reference lines on the side walls are set accordingly. Or in other cases, the 3D virtual teeth are horizontally arranged with the centers of the standardly bonded brackets on the same horizontal line and the root-shaped connectors fixed to the connecting grooves, and the horizontal reference lines on the side walls are set accordingly.

Generally speaking, in the current orthodontic training, the present invention can be applied in the evaluation of brackets used in the straight-wire technique, HX brackets, ROTH brackets, and edgewise technique. It should be noted that the examples provided should not be construed as limiting the protection scope of the present invention. Any orthodontic treatment involves a combination of brackets and archwire where the positions of the brackets abide by a certain standard should still fall within the protection scope of the present invention.

Wherein, an identification area is also set on the evaluation base for QR scan.

In addition, in order to cooperate with digital training, the computer-aided evaluation method of bracket bonding accuracy based on the digital image correlation technology-facilitated comparison algorithm processing can also be applied to the present invention. To better explain the present invention, we provide a digital image capturing device for digital image comparison algorithm:

The photographing equipment applied to the device above is a box with a device for evaluating the bracket bonding accuracy fixed at one end of the inner side of the box. A photographing device is placed at the opposing side of the box, and the distance between the device and the photographing device is 10-40 cm.

Wherein, in the device for evaluating the bracket bonding accuracy, a calibration mark is also set on the evaluation base, which is used for calibration after shooting or imaging. Preferably, the calibration mark has a "+" shape, "L" shape, or "#" shape formed by horizontal lines and vertical lines.

Generally speaking, the photographing device is a digital camera or a mobile phone.

Generally speaking, the photographing device is required to provide a clear image of the device, and therefore auxiliary photographing equipment can also be utilized according to actual scenarios, under the premise that the equipment cause no harm to the accuracy of the imaging.

When the aforementioned digital image comparison algorithm is applied, the view of the imaging device is considered the evaluation view. By evaluating the distortion or deviation of the calibration mark set on the evaluation base on the photo, the accuracy of the digital photo can be evaluated. Once the accuracy of the digital image is determined, an automatic measure of the translation and rotation between the bonded bracket and the SBR can be carried out according to the reference lines and/or the color stamp on the evaluation base. Moreover, the accuracy of bracket bonding can be automatically evaluated and scored by comparing the translation and rotation with the score sheet for evaluation.

In addition, according to the QR code on the evaluation base, the evaluation scoring result can be automatically included in the corresponding file of the QR code by the computer.

The present invention has the following benefits:

1. Users can evaluate the accuracy of bracket bonding after performing the bonding training easily and rapidly, which significantly improves the efficiency of orthodontic training.

2. Users can disassemble the virtual teeth on the evaluation base at will and install them on the dental base which simulates the bracket bonding process in the oral cavity. After bracket bonding, they can also disassemble the virtual teeth and place them on the evaluation base for rapid evaluation of the bracket bonding accuracy through the reference lines set on the evaluation base.

3. The present invention can simulate the oral condition for bracket bonding training. On the one hand, it helps the trainees obtain comprehensive clinical experience through training. On the other hand, it facilitates the establishment of clinical training models for typical dental malformations. In this way, the present invention plays an important part in the cultivation of next-generation orthodontists.

4. The present invention can also be directly combined with the comparison algorithm processing of the digital image correlation technology. The accuracy of the bracket bonding can be digitally analyzed and evaluated rapidly through the image processing algorithm, saving time and guaranteeing the accuracy of the evaluation process.

1 virtual tooth, 1-1 virtual crown, 1-2 root-shaped connector, 1-3 hollow structure, 2 evaluation base, 3 connecting groove, 4 side wall, 5-1 horizontal reference line, 5-2 vertical reference line, 5-3 tooth long axis (TA) reference line, 6 standard bonding region (SBR), 6-1 SBR center, 7 tooth long axis, 8 calibration mark, 9 QR code label, 10 bracket, 11 transparent plate.

DETAILED DESCRIPTION OF THE EMBODIMENTS

The present invention will be further described below through examples in conjunction with the accompanying drawings. It should be noted that the examples provided should not be construed as limiting the protection scope of the present invention, and some non-essential improvements and adjustments made to the present invention by those skilled in the art based on the content of the present invention should still fall within the protection scope of the present invention.

Example 1

Figure 1:
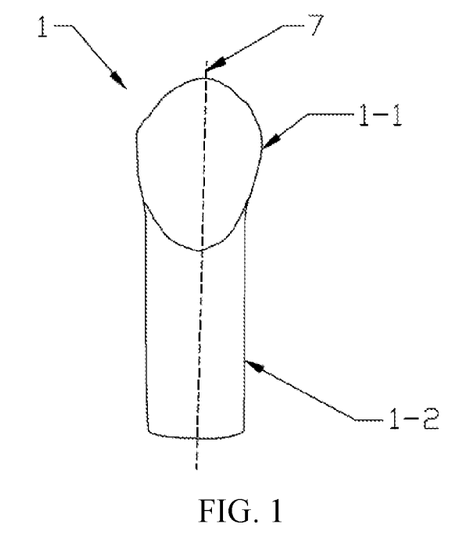
FIG. 1 illustrates the structure of the virtual tooth in example 1, wherein the virtual tooth represents the human tooth 23, wherein the dotted straight line denotes the long axis of the virtual tooth.
Figure 2:
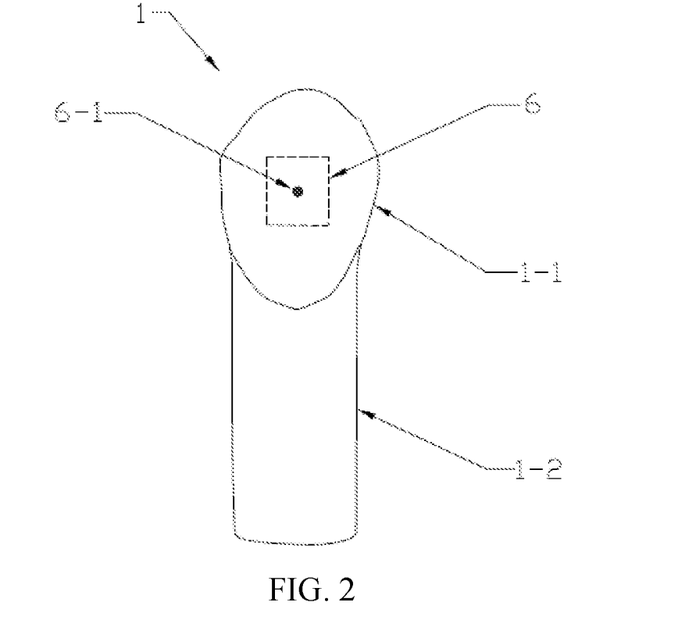
FIG. 2 illustrates the structure of the virtual tooth in example 1, wherein the virtual tooth represents the human tooth 23, wherein the dotted bordered rectangle denotes the standard bonding region (SBR), the solid point in the rectangle denotes the SBR center.
Figure 3:
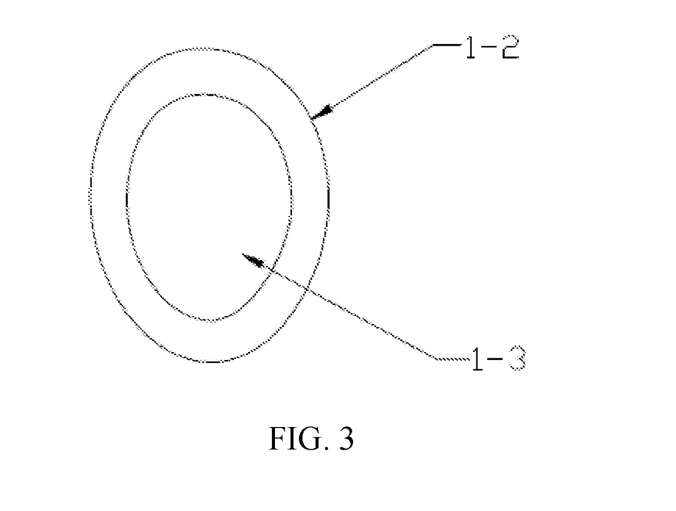
FIG. 3 illustrates the cross-section of the root-shaped connector on the virtual tooth in example 1, wherein the shape of the cross-section is in accordance with that of the virtual tooth at 1 mm apically from the cement-enamel junction (CEJ) along the tooth long axis, wherein the cross-section is hollow.
Figure 4:
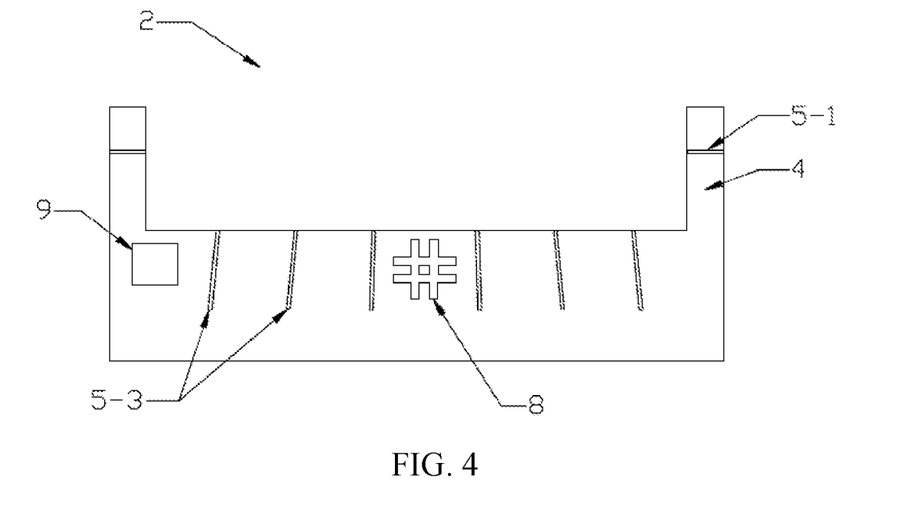
FIG. 4 illustrates the structure of the evaluation base in example 1.
Figure 5:
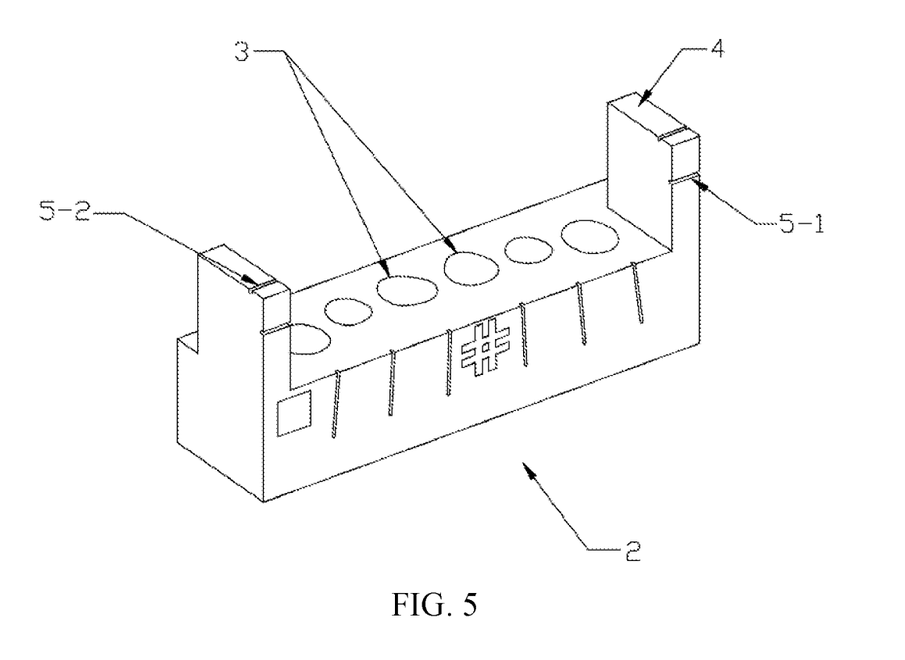
FIG. 5 illustrates the three-dimensional (3D) structure of the evaluation base in example 1.
Figure 6:
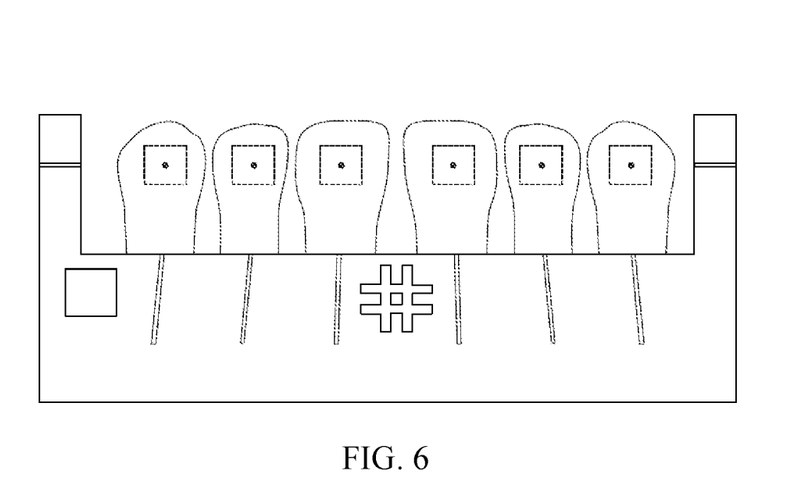
FIG. 6 illustrates the evaluation base with the virtual teeth fixed in example 1, wherein the dotted bordered rectangles denote the SBRs, and the solid points within the rectangles denote the SBR centers. The intersections of the reference lines on the evaluation base and the extended lines of the tooth long axis (TA) reference lines overlap with the corresponding SBR center.
Figure 7:
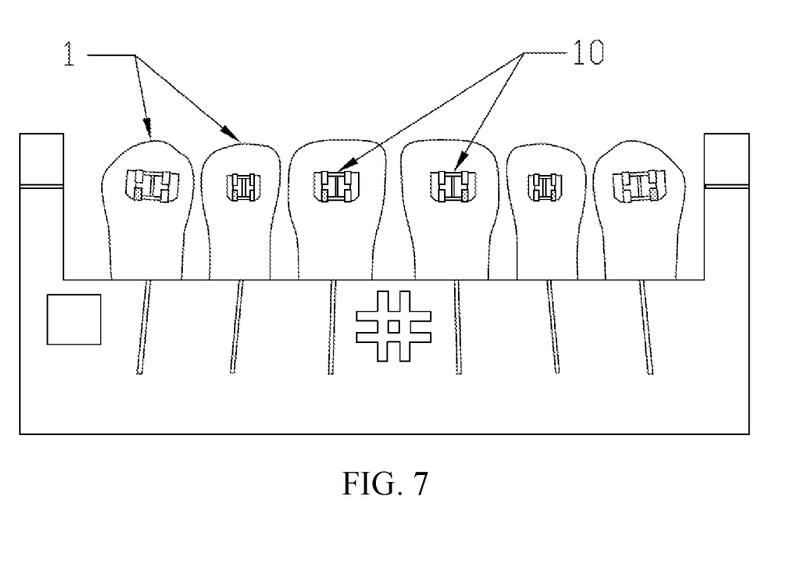
FIG. 7 illustrates the evaluation base with the virtual teeth fixed in example 1, wherein the brackets have been bonded on the virtual teeth in standard positions. Obviously, the vertical slots of the brackets overlap with the corresponding extended lines of the TA reference lines.
Figure 8:
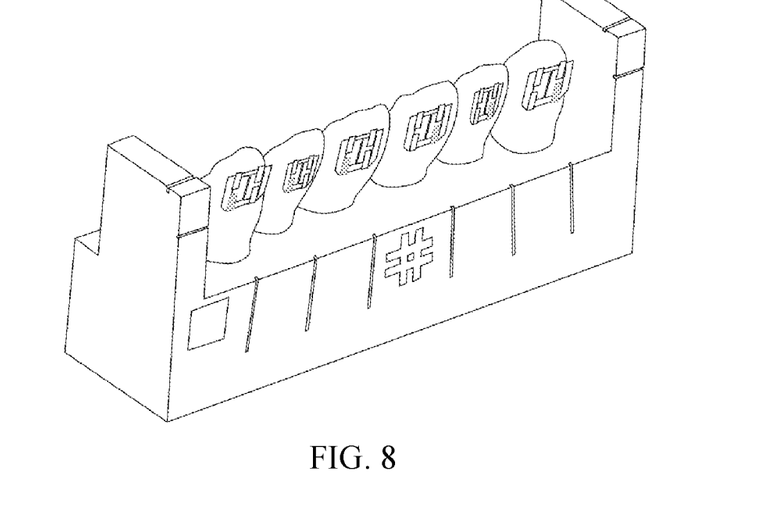
FIG. 8 illustrates the three-dimensional structure of the evaluation base with the virtual teeth fixed to it in example 1. Obviously, the reference lines on the side walls of the evaluation base can be used to evaluate the position of bracket bonding.

This example includes the following device and the supporting evaluation method in training:

FIG. 1 to FIG. 8 illustrate a training device for evaluating the bonding accuracy of orthodontic brackets, including virtual teeth 1 with root-shaped connectors and an evaluation base 2 to fix the virtual teeth;

the virtual tooth 1 with the root-shaped connector includes a virtual crown 1-1 and a root-shaped connector 1-2;

the six virtual crowns 1-1 have the same shape with teeth 11, 12, 13, 21, 22, 23, respectively; each virtual crown is cut at 1 mm apically from the cement-enamel junction (CEJ) along the tooth long axis, and the root-shaped connector 1-2 is merged at the cross-section;

the cross-sectional shape of the root-shaped connector 1-2 is in accordance with that of the virtual crown 1-1 and is 10 mm apically from the cross-section of the virtual crown; the root-shaped connector is hollow and has a wall of 1.5-mm thickness, with an opening on the apical side of the connector;

the evaluation base 2 includes connecting grooves 3 to fix the virtual teeth and reference lines for evaluation;

the evaluation base 2 is a cuboid with a length of 6.5 cm, a width of 2.0 cm, and a height of 1.5 cm; there are connecting grooves 3 on the top surface and side walls 4 bilateral to the connecting grooves with a height of 1.5 cm; one rectangular surface of the evaluation base is set as the frontal surface and is to the front view of evaluation;

the connecting grooves 3 are horizontally arranged and are in accordance with the root-shaped connectors 1-2, respectively; frictions exist when the virtual teeth 1 are fixed to the connecting grooves 3 but do not impede the removal of the virtual tooth;

the six connecting grooves 3 are in accordance with root-shaped connectors 1-2 of the virtual teeth, respectively; the angles between the central lines of the connecting grooves 3 and the vertical line were 6°, 5°, 2°, 2°, 5°, and 6°, respectively, i.e., the left three virtual teeth mirror the right three with angels with same values but opposite directions; in this way, when the virtual teeth 1 are fixed to the evaluation base, the crown surfaces for bracket bonding are in the same direction of the frontal surface of the evaluation base.

the evaluation reference lines include the horizontal reference lines 5-1, vertical reference lines 5-2, and the tooth long axis (TA) reference lines 5-3;

on the side walls 4, the evaluation reference lines include the horizontal reference lines 5-1 on the frontal surface of the side walls and the vertical reference lines 5-2 on the top surface of the side walls;

the TA reference lines 5-3 are on the frontal surface of the evaluation base 2, directly anterior to the connecting grooves 3;

the standard bonding region (SBR) is defined as a rectangular area designated by 2 mm up, down, left, and right from the center point of the labial or buccal surface of the virtual tooth; the SBRs of six virtual teeth are horizontally arranged when the virtual teeth 1 are fixed to the evaluation base 2; the extended lines of the reference lines pass through the SBR center 6-1, and the extended lines of the TA reference lines overlap with the corresponding tooth long axes 7 from the front view; the point of intersection of the horizontal reference lines and the extended lines of the TA reference lines define the evaluation points, and the evaluation points overlap with the corresponding SBR centers 6-1 of the virtual teeth from the front view;

in the present example, the reference lines for evaluation are the thin linear grooves on the evaluation base;

calibration mark 8 is set on the frontal surface of the evaluation base 2 with the shape of "#" constituted by two horizontal lines and two vertical lines;

QR code 9 is also set on the frontal surface of the evaluation base 2.

The evaluation method using the devices in this example includes the following steps:

(1) fix the virtual teeth 1 to the matching dental base;

(2) bond the brackets on the fixed virtual teeth 1 from step (1);

(3) remove virtual teeth 1 bonded with brackets 10 from the dental base, and fix them to the corresponding connecting grooves 3 on the evaluation base 2;

(4) determine the center points of the bonded brackets 10 on the fixed virtual teeth 1, wherein the translation is defined by the distance between the center point of the bonded bracket 10 and the evaluation point from the front view, and the rotation is defined by the angle between the vertical bracket slot and the TA reference line from the front view;

(5) evaluate bracket bonding accuracy based on the translation and the rotation.

The bracket bonding is rated as qualified when the translation of the bonded bracket from the evaluation point is below 1.0 mm and unqualified otherwise; the bracket bonding is rated as qualified when the rotation of the bonded bracket from the vertical line is below 5° and unqualified otherwise.

Example 2

Figure 9:
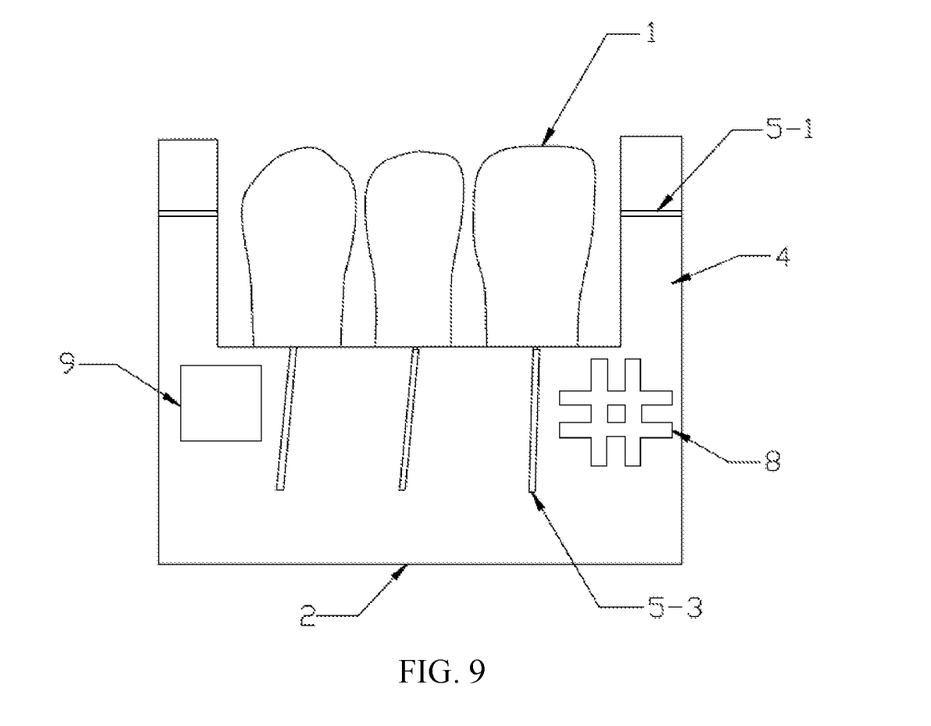
FIG. 9 illustrates the evaluation base with the virtual teeth fixed to it in example 2.

This example includes the following device and the supporting evaluation method in training:

FIG. 9 illustrates a training device for evaluating the bonding accuracy of orthodontic brackets, including virtual teeth 1 with root-shaped connectors and an evaluation base 2 to fix the virtual teeth;

the virtual tooth 1 with the root-shaped connector includes a virtual crown 1-1 and root-shaped connectors 1-2;

the three virtual crowns have the same shapes with teeth 21, 22, 23, respectively; each virtual crown is cut at the cement-enamel junction (CEJ), and the root-shaped connector is merged at the cross-section;

the cross-sectional shape of root-shaped connector is in accordance with that of the virtual crown and is 10 mm apically from the cross-section of the virtual crown; the root-shaped connector is hollow and has a wall of 1.5-mm thickness, with an opening on the apical side of the connector;

the evaluation base 2 includes connecting grooves to fix the virtual teeth and reference lines for evaluation;

the evaluation base 2 is a cuboid with a length of 3.5 cm, a width of 2.0 cm, and a height of 1.5 cm; there are connecting grooves on the top surface and side walls 4 bilateral to the connecting grooves with a height of 1.5 cm; one rectangular surface of the evaluation base is set as the frontal surface and is to the front view of evaluation;

the connecting grooves are horizontally arranged and are in accordance with the corresponding root-shaped connectors; frictions exist when the virtual teeth 1 are fixed to the connecting grooves 3 but do not impede the removal of the virtual tooth;

the three connecting grooves are in accordance with three root-shaped connectors of the virtual teeth, respectively; the angles between the central lines of the connecting grooves and the vertical lines are 6°, 5°, and 2°, respectively; in this way, when the virtual teeth are fixed to the evaluation base, the crown surfaces for bracket bonding are in the same direction of the frontal surface of the evaluation base.

the evaluation reference lines include the horizontal reference lines 5-1, vertical reference lines 5-2, and the tooth long axis (TA) reference lines 5-3;

on the side walls 4, the evaluation reference lines include the horizontal reference lines 5-1 on the frontal surface of the side walls and the vertical reference lines 5-2 on the top surface of the side walls;

the TA reference lines 5-3 are on the frontal surface of the evaluation base 2, directly anterior to the connecting grooves 3;

in the present example, the reference lines for evaluation are the thin linear grooves on the evaluation base;

the standard bonding region (SBR) is defined as a rectangular area designated by 2 mm up, down, left, and right from the center point of the labial or buccal surface of the virtual tooth; the SBRs of three virtual teeth are horizontally arranged when the virtual teeth are fixed to the evaluation base; the extended lines of the reference lines pass through the SBR center, and the extended line of the TA reference line overlaps with the corresponding tooth long axis from the front view; the point of intersection of the horizontal reference line and the extended line of the TA reference line defines the evaluation point, and the evaluation point overlaps with the SBR center of the virtual tooth from the front view;

calibration mark 8 is set on the frontal surface of the evaluation base 2 with the shape of "#" constituted by two horizontal lines and two vertical lines;

QR code 9 is also set on the frontal surface of the evaluation base 2.

The evaluation method using the devices in this example includes the following steps:

(1) fix the virtual teeth 1 to the corresponding grooves on the evaluation base;

(2) bond the bracket on the fixed virtual teeth 1 from step (1);

(3) determine the center points of the bonded brackets 10 on the fixed virtual teeth 1, wherein the translation is defined by the distance between the center point of the bonded bracket 10 and the evaluation point from the front view, and the rotation is defined by the angle between the vertical bracket slot and the TA reference line from the front view;

(4) evaluate bracket bonding accuracy based on the translation and the rotation.

The bracket bonding is rated as qualified when the translation of the bonded bracket from the evaluation point is below 1.0 mm and unqualified otherwise; the bracket bonding is rated as qualified when the rotation of the bonded bracket from the vertical line is below 5° and unqualified otherwise.

Example 3

Figure 10:
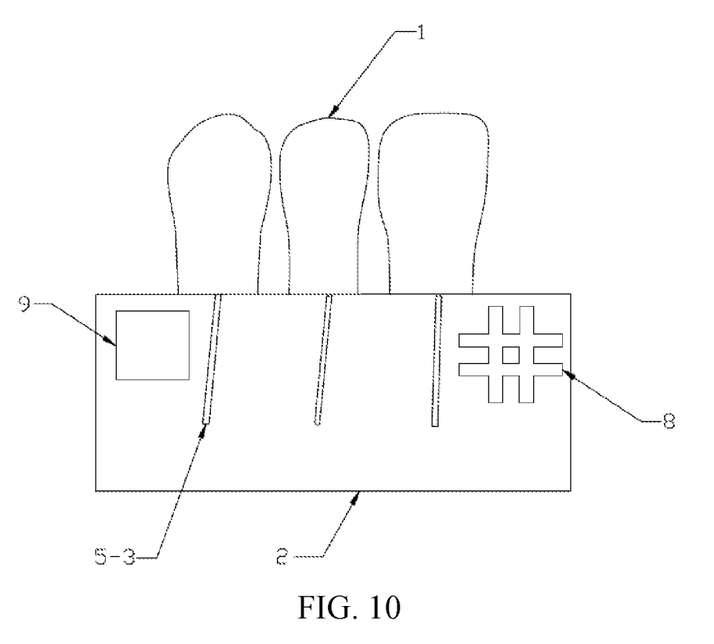
FIG. 10 illustrates the evaluation base with the virtual teeth fixed to it in example 3.
Figure 11:
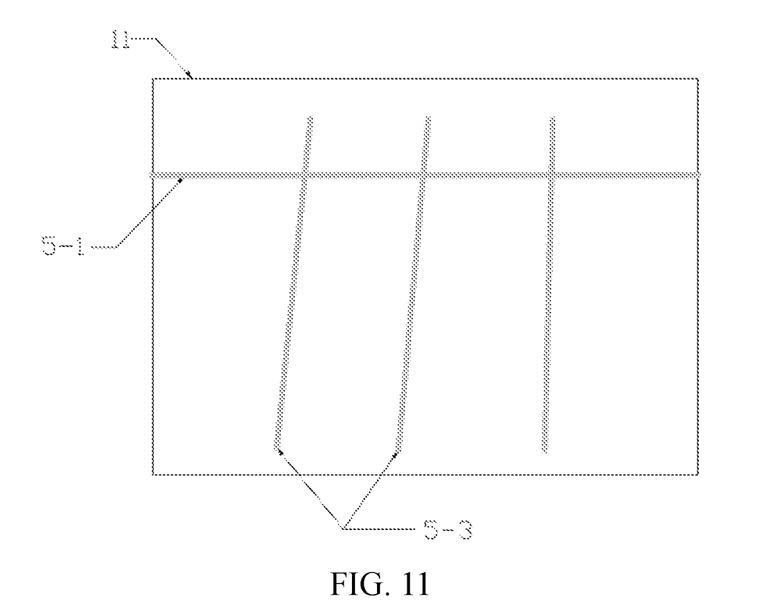
FIG. 11 illustrates the transparent plate in example 3.
Figure 12:
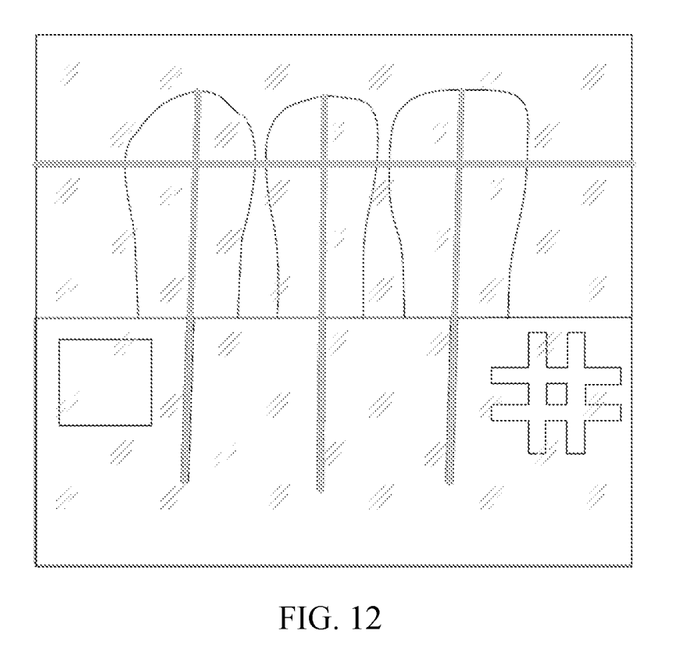
FIG. 12 illustrates the evaluation base with the virtual teeth fixed to it and the transparent plate in example 3.

This example includes the following device and the supporting evaluation method in training:

FIG. 10 to FIG. 12 illustrate a training device for evaluating the bonding accuracy of orthodontic brackets, including virtual teeth 1 with root-shaped connectors and an evaluation base 2 to fix the virtual teeth;

the virtual tooth 1 with the root-shaped connector includes a virtual crown and root-shaped connectors;

the three virtual crowns have the same shape with teeth 21, 22, and 23, respectively; each virtual crown is cut at the cement-enamel junction (CEJ), and the root-shaped connector is merged at the cross-section;

the cross-sectional shape of the root-shaped connector 1-2 is in accordance with that of the virtual crowns and is 10 mm apically from the cross-section of the virtual crown; the root-shaped connector is hollow and has a wall of 1.5-mm thickness, with an opening on the apical side of the connector;

the evaluation base 2 includes connecting grooves to fix the virtual teeth and reference lines for evaluation;

the evaluation base 2 is a cuboid with a length of 3.5 cm, a width of 2.0 cm, and a height of 1.5 cm; there are connecting grooves on the top surface; one rectangular surface of the evaluation base is set as the frontal surface and is to the front view of evaluation;

the connecting grooves 3 are horizontally arranged and are in accordance with the root-shaped connectors 1-2, respectively; frictions exist when the virtual teeth 1 are fixed to the connecting grooves 3 but do not impede the removal of the virtual tooth;

the six connecting grooves 3 are in accordance with root-shaped connectors 1-2 of the virtual teeth, respectively; the angles between the central lines of the connecting grooves 3 and the vertical line were 6°, 5°, and 2°, respectively; in this way, when the virtual teeth 1 are fixed to the evaluation base, the crown surfaces for bracket bonding are in the same direction of the frontal surface of the evaluation base.

the TA reference lines 5-3 are on the frontal surface of the evaluation base 2, directly anterior to the connecting grooves;

in the present example, the TA reference lines are the thin linear grooves on the evaluation base 2;

the evaluation base also includes a transparent plate with a length of 3.5 cm and a width of 3 cm; horizontal reference lines 5-1 and vertical reference lines 5-3 are set on the transparent plate 11; since it has the same length as the evaluation base, it can be seated on the frontal surface of the evaluation base; the accuracy of bracket bonding can be assessed by superimposing the TA reference lines 5-3 on the transparent plate with the TA reference lines on the evaluation base, the standard bonding region (SBR) is defined as a rectangular area designated by 2 mm up, down, left, and right from the center point of the labial or buccal surface of the virtual tooth; the SBRs of six virtual teeth are horizontally arranged when the virtual teeth 1 are fixed to the evaluation base 2; when the transparent plate is seated, the horizontal lines pass through the SBR center, the TA reference lines overlap with the tooth long axes on the corresponding virtual teeth from the view of evaluation; additionally, the intersections of the horizontal reference lines and the TA reference lines define the evaluation points, and the evaluation points overlaps with the corresponding SBR center of the virtual tooth from the view of evaluation;

calibration mark 8 is set on the frontal surface of the evaluation base 2 with the shape of "#" constituted by two horizontal lines and two vertical lines;

QR code 9 is also set on the frontal surface of the evaluation base 2.

The evaluation method using the devices in this example includes the following steps:

(1) fix the virtual teeth 1 to the corresponding grooves on the evaluation base;

(2) bond the bracket on the fixed virtual teeth 1 from step (1);

(3) determine the center points of the bonded brackets 10 on the fixed virtual teeth 1, wherein the translation is defined by the distance between the center point of the bonded bracket 10 and the evaluation point from the front view, and the rotation is defined by the angle between the vertical bracket slot and the TA reference line from the front view;

(4) evaluate bracket bonding accuracy based on the translation and the rotation.

The bracket bonding is rated as qualified when the translation of the bonded bracket The bracket bonding is rated as qualified when the translation of the bonded bracket from the evaluation point is below 1.0 mm and unqualified otherwise; the bracket bonding is rated as qualified when the rotation of the bonded bracket from the vertical line is below 5° and unqualified otherwise.

Example 4

Figure 13:
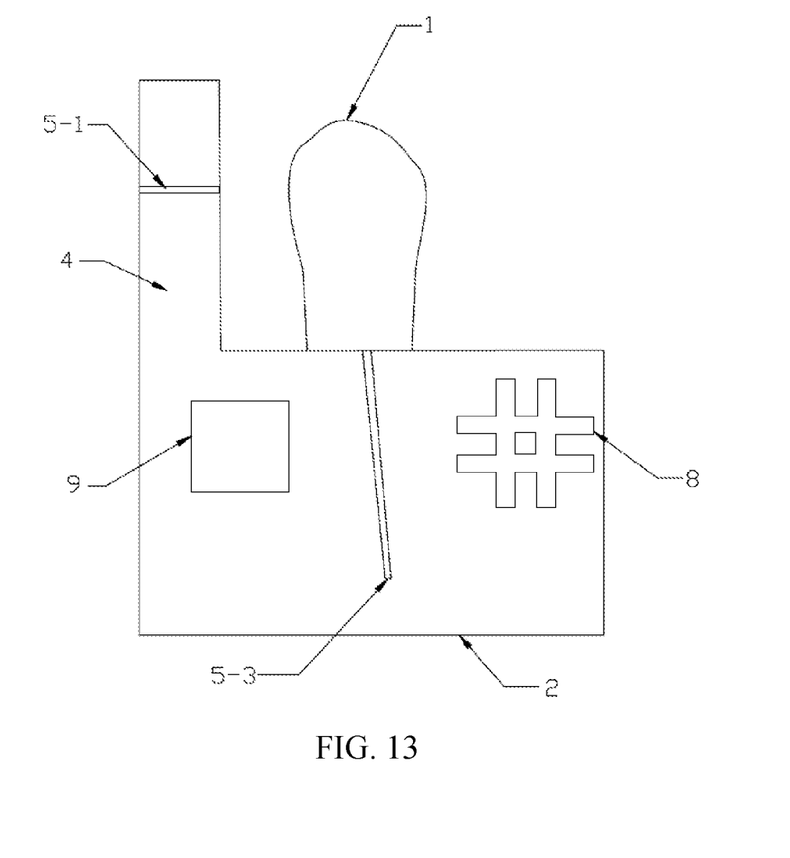
FIG. 13 illustrates the evaluation base with the virtual teeth fixed to it in example 4.

This example includes the following device and the supporting evaluation method in training:

FIG. 13 illustrates a training device for evaluating the bonding accuracy of orthodontic brackets, including virtual tooth 1 with a root-shaped connector and an evaluation base 2 to fix the virtual tooth;

the virtual tooth 1 with the root-shaped connector includes a virtual crown and a root-shaped connector;

the virtual crown has the same shape with the tooth 44; the virtual crown is cut at the cement-enamel junction (CEJ), and the root-shaped connector is merged at the cross-section;

the cross-sectional shape of root-shaped connector is in accordance with that of the virtual crown and is 10 mm apically from the cross-section of the virtual crown; the root-shaped connector is hollow and has a wall of 1.5-mm thickness, with an opening on the apical side of the connector;

the evaluation base 2 includes a connecting groove to fix the virtual tooth and reference lines for evaluation;

the evaluation base 2 is a cuboid with a length of 2.5 cm, a width of 1.5 cm, and a height of 1.5 cm; there is a connecting groove on the top surface and a side wall 4 lateral to the connecting groove with a height of 1.5 cm; one rectangular face of the evaluation base is set as the frontal surface and is to the front view of evaluation;

the connecting groove is in accordance with the root-shaped connector; friction exists when the virtual tooth 1 is fixed to the connecting groove but does not impede the removal of the virtual tooth, the one connecting grooves is in accordance with root-shaped connector of tooth 44; the angle between the central line of the connecting groove and the vertical line is 6°; in this way, when the virtual tooth is fixed to the evaluation base, the crown surface for bracket bonding is in the same direction of the frontal surface of the evaluation base.

the evaluation reference lines include the horizontal reference line 5-1, vertical reference line 5-2, and the tooth long axis (TA) reference line 5-3;

on the side walls 4, the evaluation reference lines including the horizontal reference line 5-1 on the frontal surface of the side wall and the vertical reference line 5-2 on the top surface of the side wall;

the TA reference line 5-3 is on the frontal surface of the evaluation base 2, directly anterior to the connecting groove;

in the present example, the reference lines for evaluation are the thin linear grooves on the evaluation base;

the standard bonding region (SBR) is defined as a rectangular area designated by 2 mm up, down, left, and right from the center point of the labial or buccal surface of the virtual tooth; the SBRs of the virtual tooth is horizontally arranged when the virtual tooth is fixed to the evaluation base; the extended lines of the reference lines pass through the SBR center, and the extended line of the TA reference line overlaps with the corresponding tooth long axis from the view of evaluation; the point of intersection of the horizontal reference line and the extended line of the TA reference line defines the evaluation point, and the evaluation point overlaps with the SBR center of the virtual tooth from the view of evaluation;

calibration mark 8 is set on the frontal surface of the evaluation base with the shape of "14" constituted by a horizontal line and a vertical line;

The evaluation method using the devices in this example includes the following steps:

(1) fix the virtual tooth 1 to the groove on the evaluation base;

(2) bond the bracket on the fixed virtual tooth 1 from step (1);

(3) determine the center point of the bonded bracket on the fixed virtual tooth, wherein the translation is defined by the distance between the center point of the bonded bracket 10 and the evaluation point from the front view, and the rotation is defined by the angle between the vertical bracket slot and the TA reference line from the front view;

(4) evaluate bracket bonding accuracy based on the translation and rotation.

The bracket bonding is rated as qualified when the translation of the bonded bracket from the evaluation point is below 1.0 mm and unqualified otherwise; the bracket bonding is rated as qualified when the rotation of the bonded bracket from the vertical line is below 5° and unqualified otherwise.

What is claimed is:

1. A bracket bonding accuracy evaluation method, comprising:

using a training device for evaluating the bonding accuracy of orthodontic brackets, wherein the training device comprises a plurality of virtual teeth and an evaluation base to fix the virtual teeth, and a manufacture procedure of the training device comprises taking impressions of selected human teeth, and generating 3D tooth models of the selected human teeth by 3D scanning;

wherein each of the virtual teeth comprises a virtual crown and a root-shaped connector fixed to the virtual crown, wherein the virtual crown has a standard bonding region (SBR) marked on the virtual crown; the root-shaped connector is merged to the virtual crown at ±1 mm from a cemento-enamal junction (CEJ), and the long axis of the root-shaped connector is parallel to the tooth long axis;

the evaluation base comprises connecting grooves to fix the virtual teeth and reference lines for evaluation, wherein the connecting grooves fit the root-shaped connectors of a virtual tooth having a corresponding shape of the plurality of virtual teeth;

each of the virtual teeth is fixed to the evaluation base through the connection between the root-shaped connector and the connecting groove, and when a plurality of virtual teeth are arranged, the plurality of virtual teeth are horizontally arranged, and crown surfaces used for bracket bonding face the same direction;

the reference lines comprise horizontal reference lines, vertical reference lines, and tooth long axis (TA) reference lines, wherein the TA reference lines are parallel to long axes of corresponding virtual teeth fixed to the evaluation base, intersections of the horizontal reference lines and the TA reference lines define evaluation points, and the evaluation points overlap with corresponding SBR centers of the virtual teeth;

the bracket bonding accuracy evaluation method further comprises steps of:

(1) fixing the virtual teeth to the evaluation base;

(2) bonding a bracket on the fixed virtual teeth from step (1);

(3) removing the virtual teeth bonded with the bracket from the matching dental base, and fixing the virtual teeth bonded with the bracket to the corresponding connecting groove on the evaluation base;

(4) determining a center point of the bonded bracket on the fixed virtual teeth, wherein a translation is defined by a distance between the center point of the bonded bracket and the evaluation point, and a rotation is defined by an angle between a vertical bracket slot and a TA reference line;

(5) evaluating the bracket bonding accuracy based on the translation and the rotation;

or (1) fixing the virtual teeth to a corresponding connecting groove on the evaluation base;

(2) bonding a bracket on the fixed virtual teeth from step (1);

(3) determining a center point of the bonded bracket on the fixed virtual teeth, wherein a translation is defined by the distance between the center point of the bonded bracket and the evaluation point, and a rotation is defined by the angle between the vertical bracket slot and the TA reference line;

(4) evaluating the bracket bonding accuracy based on the translation and the rotation.

2. The bracket bonding accuracy evaluation method of claim 1 wherein the SBR of each of the virtual teeth has a rectangular area that is 2 mm up, 2 mm down, 2 mm left, and 2 mm right from a center point of a labial or buccal surface of each of the virtual teeth.

3. The bracket bonding accuracy evaluation method of claim 2 wherein angles between center lines of connecting grooves and the vertical reference lines are selected according to the type of the virtual teeth; and the angles range from 0° to 20° for anterior teeth and 15° to 45° for posterior teeth.

4. The bracket bonding accuracy evaluation method of claim 2 wherein the evaluation points overlap with the corresponding SBR centers of the virtual teeth in a horizontal direction when the virtual teeth are fixed in the connecting grooves on the evaluation base.

5. The bracket bonding accuracy evaluation method of claim 4 wherein the evaluation base is in a shape of a cuboid with the connecting grooves to fix the virtual teeth on a top surface;

the evaluation base has side walls bilateral to the connecting grooves, and the side walls are marked with the reference lines.

6. The bracket bonding accuracy evaluation method of claim 5, wherein the evaluation base is a cuboid with a length of 5-80 mm, a width of 5-30 mm, and a height of 13-40 mm; there are the connecting grooves on the top surface and the side walls bilateral to the connecting grooves with heights of 7-15 mm.

7. The bracket bonding accuracy evaluation method of claim 5, wherein a cross-sectional shape of the root-shaped connector corresponds to the cross-sectional shape of each of the virtual teeth at ±1 mm from the CEJ along the tooth long axis, and the length of the root-shaped connector is 10-15 mm along the tooth long axis.

* * * * *